(12) United States Patent
Sommer et al.

(10) Patent No.: US 10,357,156 B2
(45) Date of Patent: Jul. 23, 2019

(54) TELEMEDICINE CONSULTATION AND DIAGNOSTIC SYSTEMS AND METHODS THEREFORE

(71) Applicant: Telepresence Technologies, LLC, Plano, TX (US)

(72) Inventors: Darren J. Sommer, Dublin, OH (US); Peter McDuffie White, McKinney, TX (US)

(73) Assignee: Telepresence Technologies, LLC, Plano, TX (US)

( * ) Notice: Subject to any disclaimer, the term of this patent is extended or adjusted under 35 U.S.C. 154(b) by 0 days.

(21) Appl. No.: 15/853,358

(22) Filed: Dec. 22, 2017

(65) Prior Publication Data

US 2018/0192875 A1   Jul. 12, 2018

Related U.S. Application Data

(60) Provisional application No. 62/443,468, filed on Jan. 6, 2017.

(51) Int. Cl.
| | |
|---|---|
| *A61B 5/00* | (2006.01) |
| *H04N 7/15* | (2006.01) |
| *G16H 40/40* | (2018.01) |
| *H04N 7/14* | (2006.01) |
| *G16H 80/00* | (2018.01) |
| *G16H 10/60* | (2018.01) |
| *G16H 40/67* | (2018.01) |

(52) U.S. Cl.
CPC ............ *A61B 5/0015* (2013.01); *A61B 5/742* (2013.01); *A61B 5/7465* (2013.01); *G16H 40/40* (2018.01); *G16H 80/00* (2018.01); *H04N 7/142* (2013.01); *H04N 7/15* (2013.01); *A61B 5/0026* (2013.01); *G16H 10/60* (2018.01); *G16H 40/67* (2018.01)

(58) Field of Classification Search
CPC ..... A61B 5/0015; A61B 5/742; A61B 5/7465; H04N 7/142; H04N 7/15; G16H 40/40; G16H 80/00
See application file for complete search history.

(56) References Cited

U.S. PATENT DOCUMENTS

| | | | |
|---|---|---|---|
| 2013/0307237 A1* | 11/2013 | Chen ..................... | A61G 12/001 280/35 |
| 2015/0305086 A1* | 10/2015 | Uttley ....................... | B62B 1/12 280/652 |

* cited by examiner

*Primary Examiner* — Leon Flores
(74) *Attorney, Agent, or Firm* — Slater Matsil, LLP

(57) ABSTRACT

A telemedicine cart includes a body with casters mounted underneath, a monitor mounted to the body, and a power supply connection coupled to the monitor. The body includes a cabinet with a hinged door for access to the interior of the cabinet when opened. A screen on the monitor has a portrait orientation and is disposed above the cabinet, in a vertical plane perpendicular to the bottom of the cabinet. The screen is longer than it is wide. The screen is longer than a height of the cabinet beneath the screen. A video of a vertically upright person displayed on the screen, will appear to be at or near an average standing height of adults to a user in front of the screen, and will appear to be life-sized or near life-sized to the user.

13 Claims, 6 Drawing Sheets

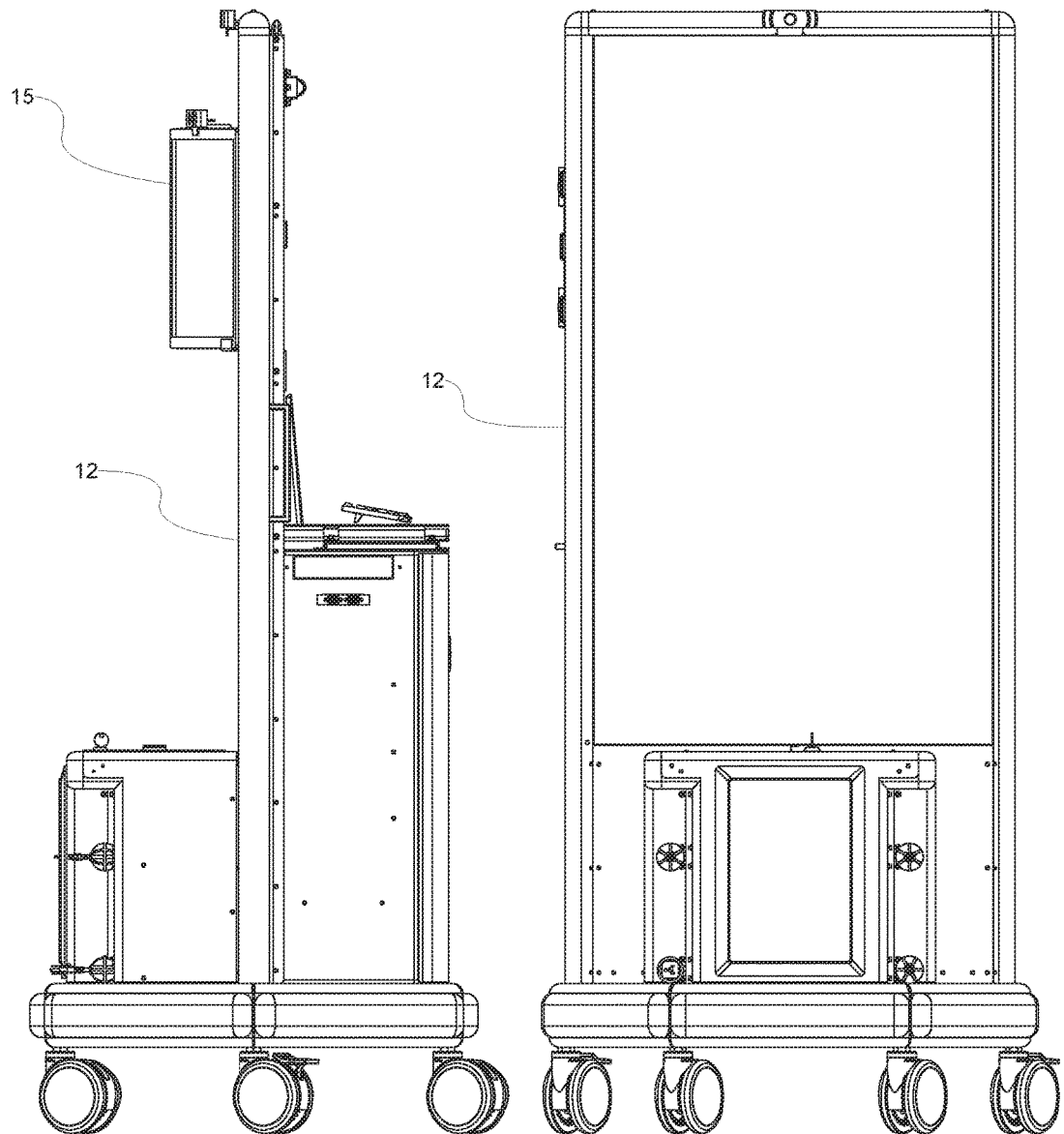

TELEMEDICINE CONSULTATION AND DIAGNOSTIC SYSTEMS AND METHODS THEREFORE

CROSS-REFERENCE TO RELATED APPLICATIONS

This application claims the benefit of U.S. Provisional Application No. 62/443,468, filed on Jan. 6, 2017, which application is hereby incorporated herein by reference.

TECHNICAL FIELD

The present invention relates to a video conference system for a medical professional to appear at life-size on a portrait oriented image display device integrated into a cart for engaging in telemedicine procedures, and methods for utilizing same.

BACKGROUND

There is a need for an improved method for physicians to provide medical services to patients through the use of a cart for practicing telemedicine. Presently some medical carts include a monitor in the landscape format for displaying an incoming image of a physician. The size of the monitor may range between 19" to 27". There is a physical limitation on the size of the monitor since the cart must not be wider than the width of a typical door. As a general rule, a cart is typically not wider than 30". While it is possible to see a physician appearing on the screen of the monitor, the physician appears much smaller than life-size. As a result, the patient cannot gain a sense of presence of the physician.

Furthermore, the physician may be transmitting from a typical video conference system or computer with a webcam. By the standard configuration of video conference systems and webcams on computer monitors, the camera is above the monitor displaying transmitted image of the room with the patient. The camera will view the physician looking downward toward the image of the patient. As a result, the transmitted camera view of the physician will appear on the patient's monitor as looking downward, instead of looking toward the patient. This will show that the physician is not engaged in a natural conversation with the patient due to the lack of perceived eye contact.

Another aspect of typical telemedicine carts is that the monitor is in the landscape orientation. This horizontal aspect ratio limits the area of the image display device that can accommodate the image of a physician. The horizontal image may be able to show the head and shoulders of the physician, but this is only a small portion of the physician's body. The result is a lack in the sense of presence due to the limited "body language" of the physician.

FIG. 1 provides a prior art example of a telemedicine cart for video conference communication between a remotely located physician and a patient within a medical facility. The telemedicine cart 4 has a monitor 2 placed on a supporting structure of a cart. The monitor 2 displays an image 1 in a landscape orientation. The image 1 of a physician is smaller than life-size, which diminishes the sense of presence. The width and height of cart 4 with monitor 2 are limited by the size of the standard opening of a door, so that the cart can be easily moved from room to room. As a result, it is not possible to accommodate a larger screen image with a larger monitor.

There is a need for an improved telemedicine cart that can also be referred to as a medical cart, to provide a greater sense of presence of the physician for the patient.

SUMMARY

According to some embodiments of the present invention, a greater sense of presence of the physician is provided by large monitor in a vertical and portrait orientated position. The large monitor is mounted on or to a cart to display the image of a live transmission of a remotely located physician. The width of the portrait oriented monitor is not greater than a monitor in a landscape orientation, as commonly used in medical carts.

The image area of a portrait oriented monitor is 3.16 times greater than the image area of a landscape monitor based on each monitor at the same width on a cart. As an example, the width of a 55" monitor in the portrait orientation, is about the same dimension as the width of a 32" monitor in the landscape orientation. The end result is an image area on a medical cart of a set width may be over three times greater with a portrait monitor compared to a landscape monitor.

The method for the delivery of professional services using a video conference system for a life-size image in a portrait orientation within a telemedicine cart may incorporate specific technical processes, equipment specifications, systems configurations and methods of operation, all further discussed herein.

BRIEF DESCRIPTION OF THE DRAWINGS

For a more complete understanding of the present invention, and the advantages thereof, reference is now made to the following descriptions taken in conjunction with the accompanying drawings, in which:

FIG. 8 illustrates a side view of a telemedicine cart, according to some embodiments; and FIG. 9 illustrates a front view of a telemedicine cart, according to some embodiments.

DETAILED DESCRIPTION OF ILLUSTRATIVE EMBODIMENTS

Figures 1, 2:
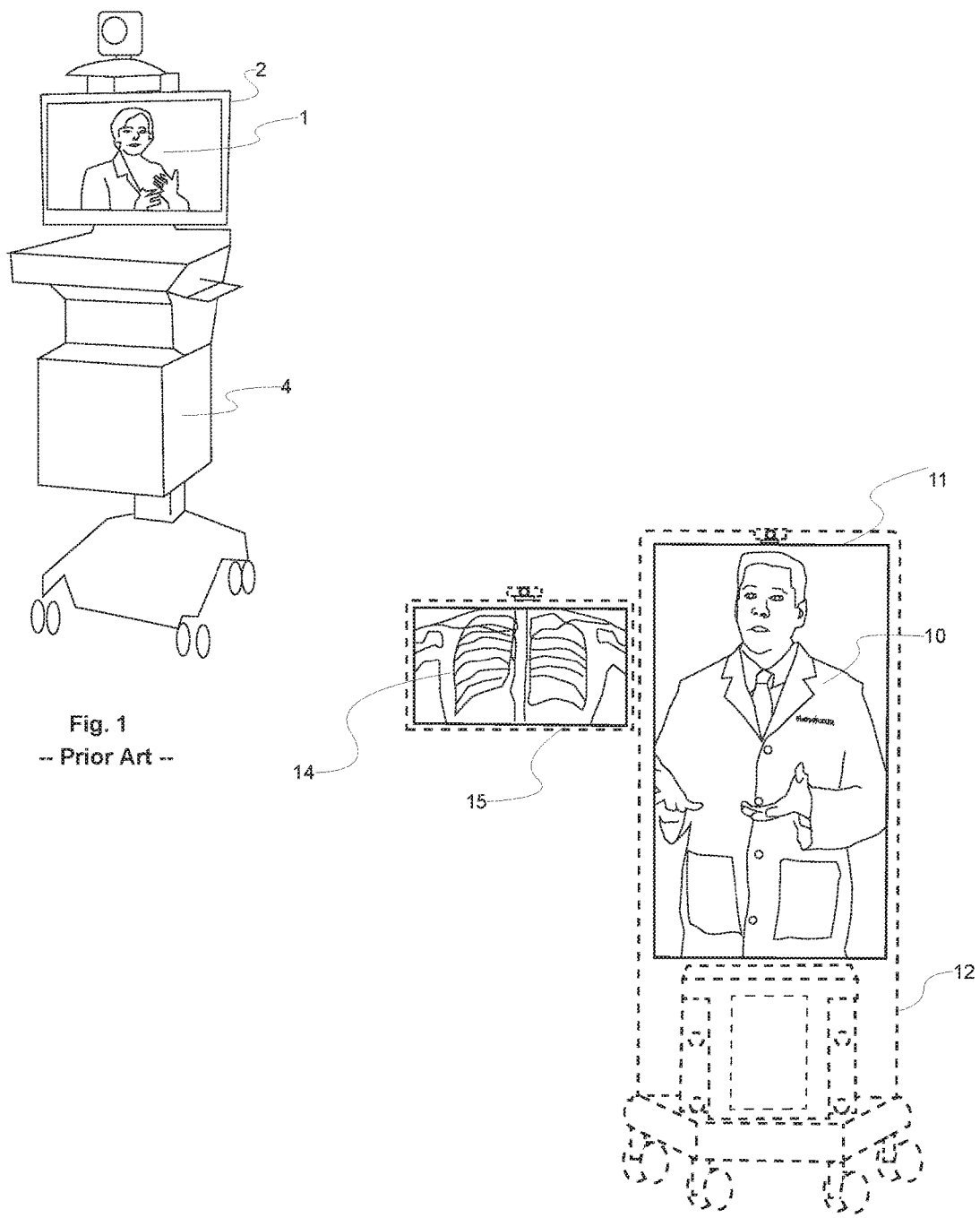
FIG. 1 illustrates a prior art configuration of a telemedicine cart with a small image of a physician on a monitor in the landscape format.
FIG. 2 illustrates a view of a telemedicine cart with a life-size image of a physician displayed in the portrait format, according to some embodiments.

The following disclosure provides different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals or letters in the various examples in the drawings and description below. This repetition is for the purpose of simplicity and clarity and does not in itself dictate a relationship between the various embodiments or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIG. 2 illustrates some embodiments of the medical cart with a large monitor 11 in a portrait orientation. The monitor 11 may vary in size, which may be in the range of 32" to 65" image display area. One preferred size is a 55" monitor. The image 10 on the monitor 11 may be of a physician displayed at life-size. The life-size image 10 may provide an optimal sense of presence as viewed by a patient. The monitor 11 may be mounted on a cart 12 with the monitor positioned so that the image 10 of the physician may be at a typical standing height. A second monitor 15 may be mounted on the side of the cart 12. This second monitor may be held in position with a hinge that will allow it to be rotated to a position on the back of the cart 12 when it is not needed for viewing from the front. The image 14 on the second monitor 15 may display the patient's medical records, supporting medical information, imagery from medical diagnostic equipment, video conferencing for additional people to participate in the session and other supporting visual collaboration activities.

Figure 3:
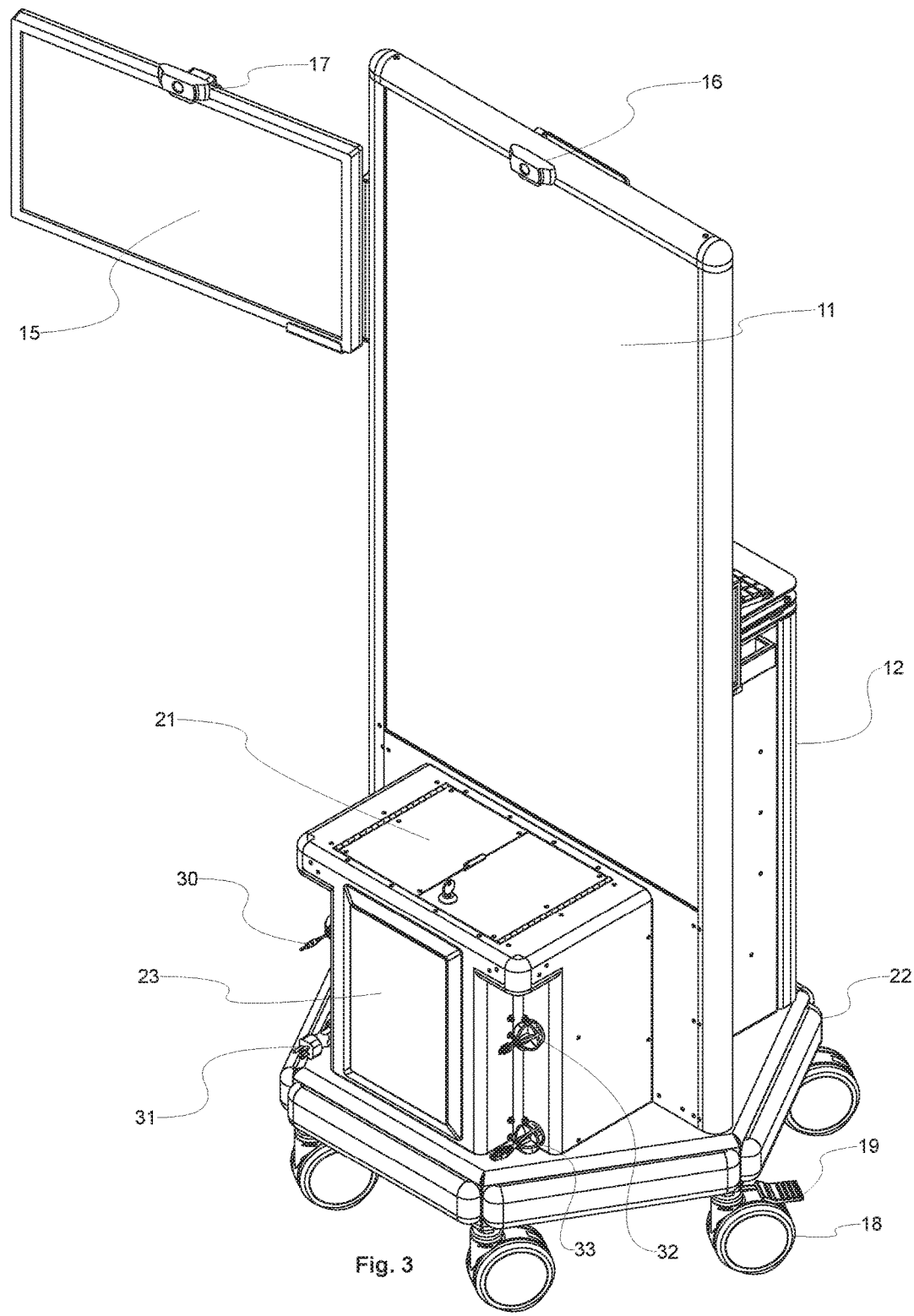
FIG. 3 illustrates a perspective view of the front of a telemedicine cart with a second monitor, according to some embodiments.

FIG. 3 illustrates front perspective view of medical cart 12, according to some embodiments. A large monitor 11 is positioned in a portrait orientation. A camera 16 is positioned at the top of the monitor 11, near the center or at the center of the frame surrounding the monitor 11. A microphone embedded in the camera 16 (not shown), is capable of capturing sound in the area in front of or around the monitor. A second monitor 15 with a camera 17 is positioned to the left of the large monitor 11. Doors 21 cover a medical diagnostic equipment cabinet. An audio speaker 23 is located at the front of the cart. The cart has retractable cable reels for mini-jack 30, AC power jack 31, mini-HDMI jack 32 and mini-Ethernet jack 33. The base of the cart has protective edge guards 22. The cart is on casters 18 with the two casters on the sides with locks 19.

Figure 4:
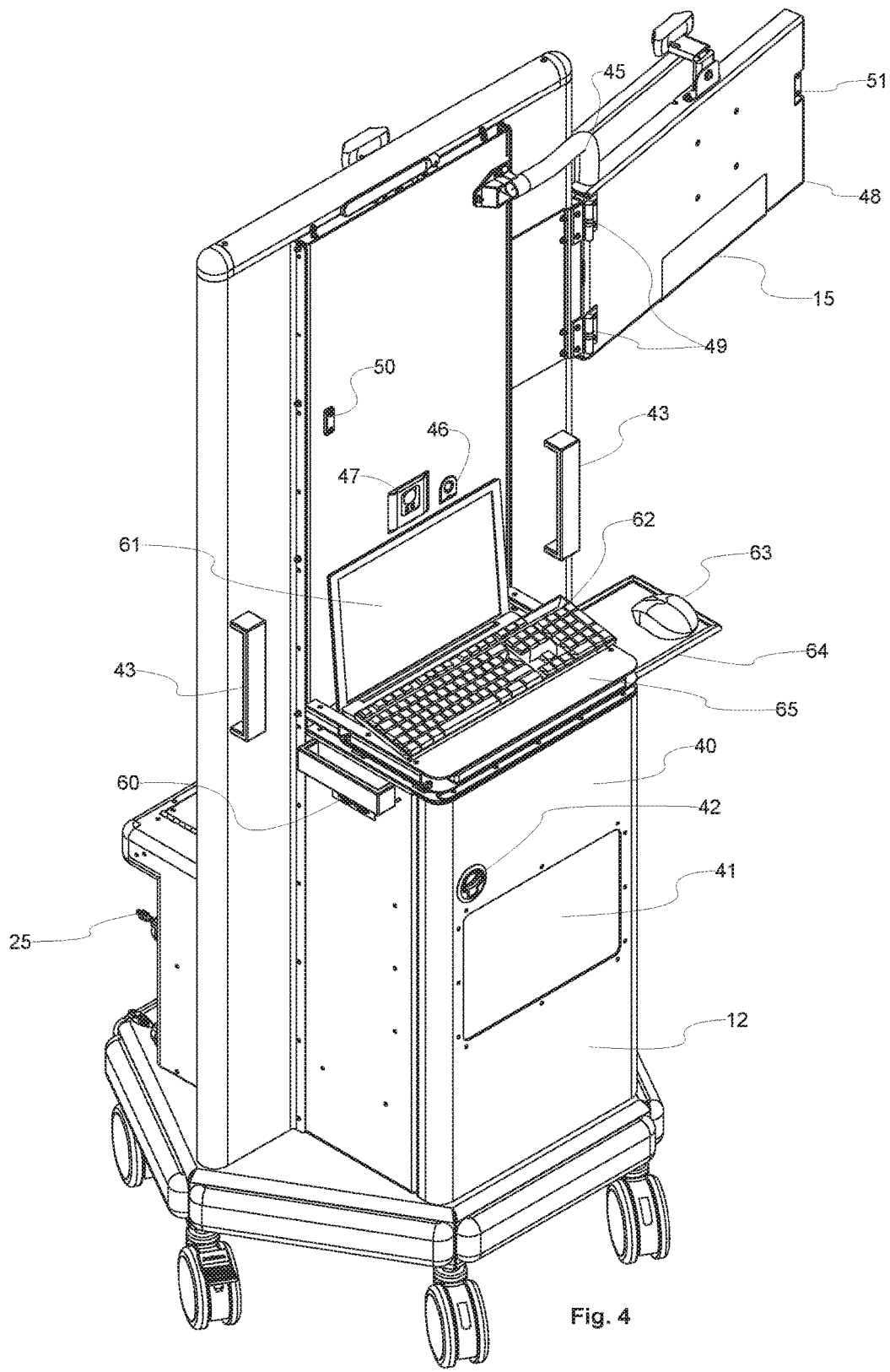
FIG. 4 illustrates a perspective view of the back of a telemedicine cart, according to some embodiments.

FIG. 4 illustrates a back perspective view of medial cart 12, according to some embodiments. A second monitor 15 has a supporting structure 48 that is attached to the medical cart 12 with hinges 49. The video and power cables are passed through a flexible cover 45. The second monitor 15 has a metal plate 51 that touches a magnet 50 to hold the second monitor 15 in position on the back of the medical cart 12 when in the closed position. Handles 43 are positioned on the two sides of the medical cart 12. A second set of handles 60 are placed on the sides of the equipment cabinet 25. The equipment cabinet 25 has a hinged door 40 with a latch 42 and a window 41 to see the equipment within the equipment cabinet 25. A laptop 61 may be positioned on top of the equipment cabinet 25 with a cover 65 to securely lock it in position. A keyboard 62 may be placed on top of the cover 65. A USB switcher 47 may be used to switch the USB connections of the keyboard 62 to multiple computers by touching the USB switch button 46. A mouse 63 may be placed on a mousepad 64 that is capable of sliding to either the right or left side of the keyboard 62 for people who are right or left handed.

According to some embodiments, the medical diagnostic equipment that is stored in the medical cart 12 is communicably connected to a communication system (for example, including the first monitor 11, the camera 16, with the microphone, the audio speaker 23, the second monitor 15 can be coupled to the communication system). The medical diagnostic equipment can be removable by any user or removable only by certain users, through the hinged doors 21. The medical diagnostic equipment can include various devices that are adapted to take a measurement on the user or on another individual, and transmit the measurement to the communication system. The communication system is adapted to transmit, to one or more remote locations, the measurements taken by the devices in the medical diagnostic equipment. The communication system is adapted to transmit live video and sound between a remote location and the user in front of the medical cart 12, including transmitting video and sound from the user in the remote location to the monitor 11 and the speaker 23, and transmitting video and sound of the user, captured by the camera 16 with its microphone, and transmit that to the remote location.

Figure 5:
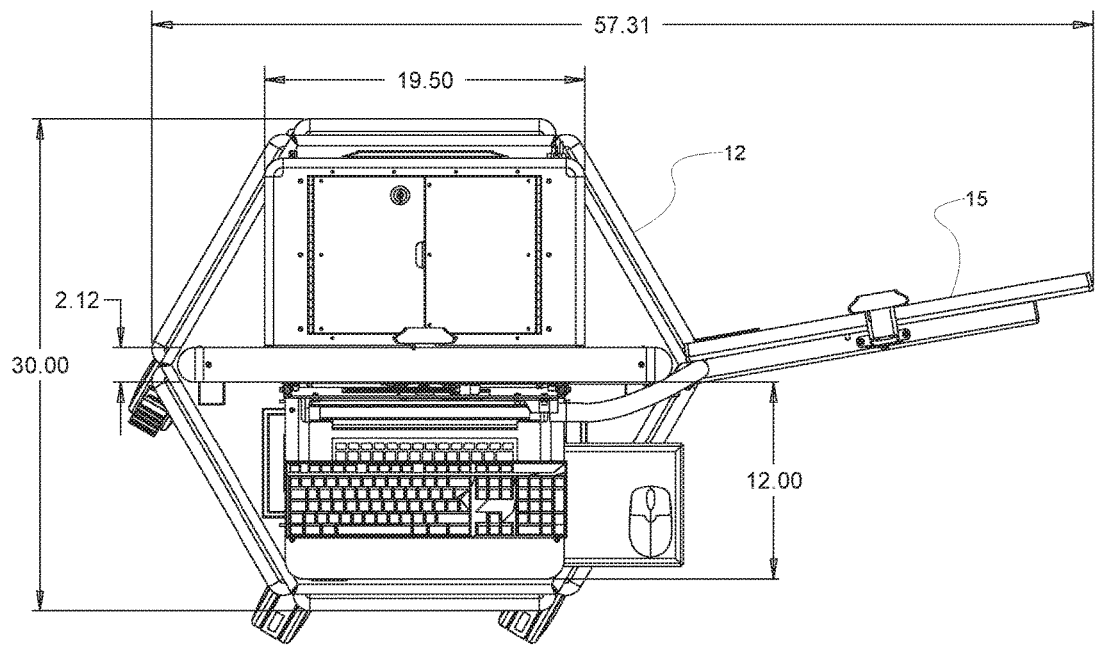
FIG. 5 illustrates a top view of a telemedicine cart, with the second monitor in position for viewing from the front, according to some embodiments.
Figure 6:
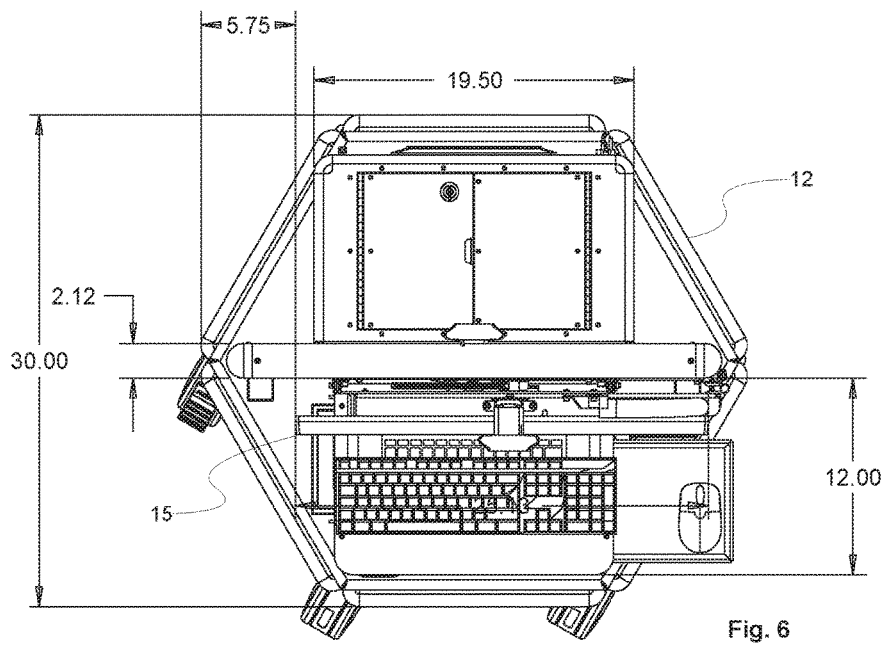
FIG. 6 illustrates a top view of a telemedicine cart, with the second monitor rotated to the back, according to some embodiments.
Figure 7:
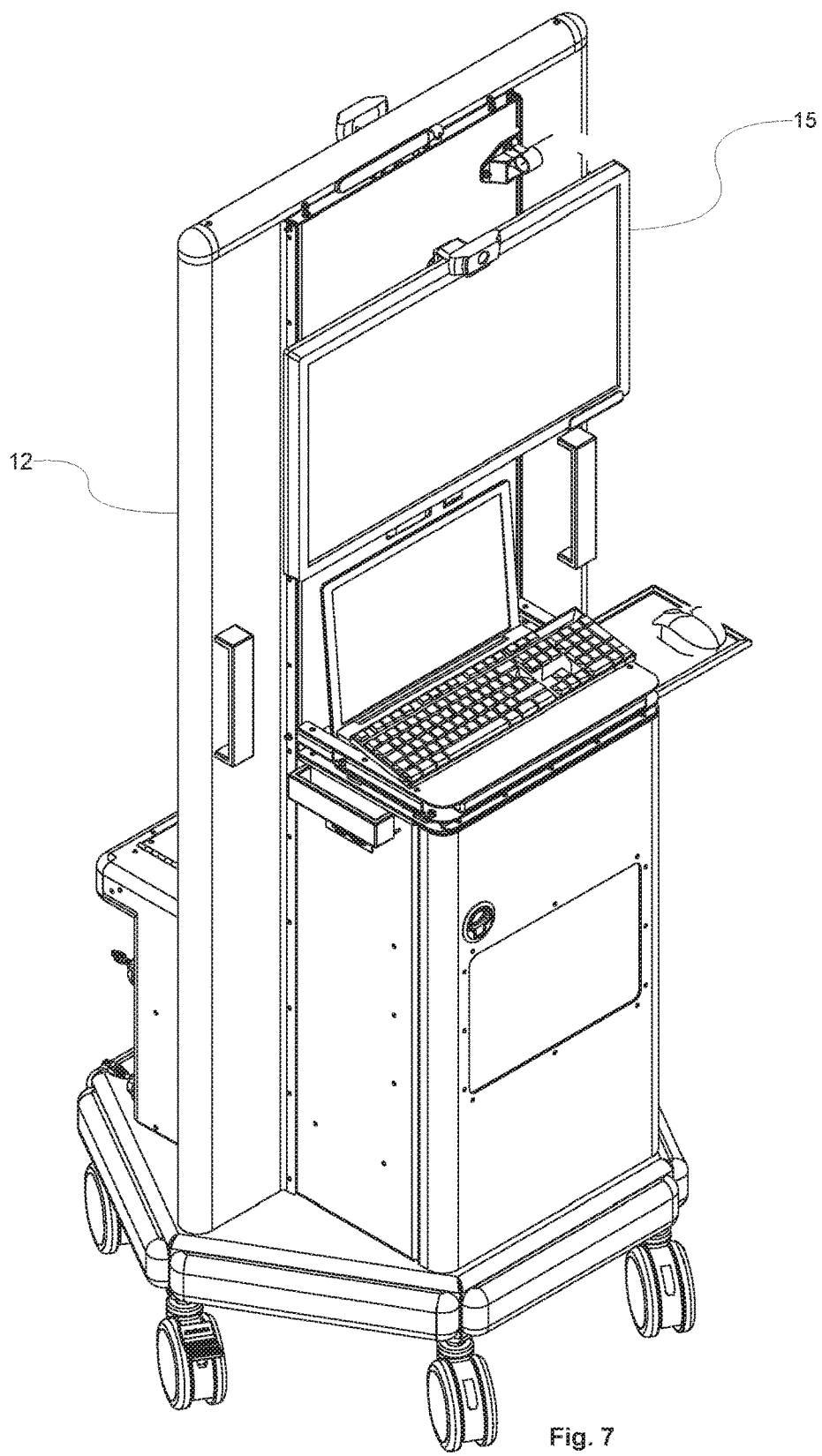
FIG. 7 illustrates a perspective view of a telemedicine cart, with the second monitor in position for viewing from the back, according to some embodiments.

Additional views are provided in FIGS. 5-9. FIG. 5 illustrates a top view of medical cart 12 with the second monitor 15 rotated to the side of the medical cart 12, according to some embodiments. FIG. 6 illustrates a top view of the medical cart 12 with the second monitor 15 rotated to the back of the medical cart 12, according to some embodiments. FIG. 7 illustrates a back perspective view of the medical cart 12 with the second monitor 15 in position at the back of the medical cart 12, according to some embodiments. FIG. 8 illustrates a side view of the medical cart 12 with the second monitor 15 in position at the back of the medical cart 12, according to some embodiments. FIG. 9 illustrates a front view of the medical cart 12, according to some embodiments.

As an example of an embodiment, monitor 11 on the medical cart 12 (also called a telemedicine cart), can display a live video to a user who is a patient, facing the medical cart 12, as a first screen on monitor 11, and through a first speaker that is on the medical cart 12. The live video may be a video captured live of a medical care provider in a remote location that is transmitted to the monitor 11 by the communication system in the medical cart 12. The cart can be wheeled around on casters 18 that have wheels inside them. The live video can appear life-sized or near life-sized to the patient who is facing the screen on monitor 11. The screen can be disposed in a portrait orientation. The medical cart 12 can include a camera and microphone embedded in the monitor 11 to capture video and audio of a patient. The communication system can then transmit the video and audio of the patient to a medical care provider in the remote location, since the communication system is coupled with monitor 11, the speaker, the camera and the microphone. The medical diagnostic device, which is stored inside the medical diagnostic equipment cart that is covered by doors 21, can be used to take a measurement of a health related feature on the patient, and can be removed through one of doors 21. The medical diagnostic device can be connected to the communication system and adapted to transmit the measurement to the medical care provider in the remote location.

The foregoing outlines features of the embodiments so that those skilled in the art may better understand the aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiment.

What is claimed is:

1. A telemedicine cart, comprising:
    a body including a cabinet, and a hinged door that encloses the cabinet when closed and that opens an interior of the cabinet to an exterior of the body when opened;
    a plurality of casters that are disposed below the body, and that are coupled to a bottom of the body;
    a first monitor mounted to the body, wherein the first monitor comprises a first screen that is disposed above the cabinet, and the first screen is disposed in a portrait orientation and in a vertical plane that is perpendicular to the bottom of the body, and that is above the cabinet; and
    a power supply connection coupled to the first monitor;
    wherein a vertical length of the first screen is larger than a width of the first screen, and the vertical length of the first screen is larger than a vertical length of the cabinet beneath the first screen; and
    wherein the first screen is adapted to display a video of a person in a vertical orientation, who appears at or near an average standing height of adults, to a user facing the first screen, when the user is positioned in front of the first screen.

2. The telemedicine cart of claim 1, wherein a size of the first screen and a height of the first screen are predefined so that the video of the person displayed on the first screen appears at or near life-size to the user, when the user is facing the first screen.

3. The telemedicine cart of claim 1, wherein each caster of the plurality of casters comprises a wheel and a double wheel, and wherein each caster of two casters further comprise a lock that, when engaged, is adapted to secure a position of the telemedicine cart.

4. The telemedicine cart of claim 1, further comprising:
    a communication system coupled to the first monitor, wherein the communication system is adapted to receive a live video of the person from a remote location, and to transmit the live video to the first monitor, wherein the live video is displayed on the first screen; and
    a speaker coupled to the communication system and to the first monitor, wherein the speaker is integrally mounted into the body, and wherein the communication system is adapted to transmit to the speaker, an audio of the live video, and the speaker is adapted to broadcast the audio received from the communication system.

5. The telemedicine cart of claim 4, wherein the first monitor comprises a frame surrounding the first screen; and wherein the telemedicine cart further comprises:
    a first camera disposed above an upper horizontal side of the first screen, and integrally mounted into the frame, wherein the first camera is adapted to capture a live video of the user when the user is positioned in from the of the first screen; and
    a first microphone mounted to the telemedicine cart, wherein the first microphone is adapted to capture sounds from the user when the user is positioned in front of the first screen; and
    wherein the first camera and the first microphone are coupled to the communication system, and the communication system is adapted to transmit back to the person in the remote location or to another remote location, the video and sounds that are captured by the first camera and the first microphone.

6. The telemedicine cart of claim 5, wherein the communication system is operable in a full duplex-mode, reducing significant interruptions or pauses caused by the sounds captured by the first microphone, onto the audio transmitted and broadcasted to the user.

7. The telemedicine cart of claim 5, further comprising a medical diagnostic device that is stored inside the cabinet, and that is communicably connected with the communication system;
    wherein the medical diagnostic device is adapted to be removable by the user or a different user through the hinged door, and take a measurement on the user or the different user, and transmit the measurement to the communication system; and
    wherein the communication system is adapted to transmit the measurement to the remote location or to a different remote location.

8. The telemedicine cart of claim 5, further comprising a second monitor hingedly attached at a vertical side of the first monitor;
    wherein the second monitor comprises a second screen and a frame, and the second screen is adapted to display a second video or a second image to the user in front of the first screen; and
    wherein the second screen can be angled along a vertical axis of the first screen.

9. The telemedicine cart of claim 8, further comprising a second camera integrally mounted to an upper horizontal side of the second monitor, wherein the second camera is adapted to capture another live video of the user when the user is in front of the first screen or the second screen.

10. The telemedicine cart of claim 8, further comprising:
    a hinge that hingedly attaches the second monitor to the frame of the first monitor;
    a metal plate attached to a back of the second monitor; and
    a magnet attached to a back of the first monitor;
    wherein the second monitor is adapted to be rotated around the hinge, when the second monitor is not in use, until the second monitor is disposed behind the first monitor; and
    wherein the second monitor is secured in place behind the first monitor by a contact of the metal plate to the magnet.

11. The telemedicine cart of claim 8, further comprising:
a plurality of retractable cables that are coupled with the first monitor or the second monitor, and that are embedded in the body, and adapted to be manually extendable from an exterior of the body;
wherein each of the plurality of retractable cables are an audio jack, a high definition multimedia interface (HDMI) jack, an alternating current (AC) power jack, or an Ethernet jack, and is adapted to be connected or coupled to the first monitor, the second monitor, or another peripheral device communicably coupled to the telemedicine cart; and
wherein the AC power jack comprises the power supply connection;
wherein the audio jack couples the first microphone to the communication system; and
wherein the Ethernet jack is adapted to provide a wired connection for the communication system to a communication network.

12. The telemedicine cart of claim 11, further comprising a cover, and the other peripheral device; wherein the other peripheral device includes a computer that is disposed above the cabinet and behind the first monitor; and wherein the cover secures the computer to the telemedicine cart.

13. A method of diagnosis comprising:
displaying a live video to a patient facing a telemedicine cart, on a first screen of a first monitor, and through a first speaker that are on the telemedicine cart, wherein the live video is a video captured live of a medical care provider in a remote location, and transmitted to the first monitor by a communication system in the telemedicine cart, wherein the first screen is in a first monitor that is disposed above a cabinet on the telemedicine cart, wherein the telemedicine cart is wheeled, wherein the live video appears life-sized or near life-sized to the patient who is facing the first screen, and wherein the first screen is disposed in a portrait orientation;
capturing video and audio of the patient through a first camera and a first microphone embedded in the first monitor;
transmitting the video and audio of the patient to the medical care provider in the remote location through a communication system that is coupled with the first monitor, the first speaker, the first camera and the first microphone; and
taking a measurement of a health related feature on the patient with a medical diagnostic device that is stored inside a cabinet on the telemedicine cart, and can be removed through a door on the cabinet, wherein the medical diagnostic device is connected to the communication system and adapted to transmit the measurement to the communication system, and the communication system is adapted to transmit the measurement to the medical care provider in the remote location.

* * * * *